(12) United States Patent
White et al.

(10) Patent No.: US 8,337,535 B2
(45) Date of Patent: Dec. 25, 2012

(54) BONE PLATE ASSEMBLY

(75) Inventors: Patrick M. White, West Chester, PA (US); Fabrice Chenaux, Exton, PA (US); Jean-Sebastien Merrette, Paoli, PA (US)

(73) Assignee: Greatbatch Medical S.A., Orvin (CH)

( * ) Notice: Subject to any disclaimer, the term of this patent is extended or adjusted under 35 U.S.C. 154(b) by 204 days.

(21) Appl. No.: 12/775,074

(22) Filed: May 20, 2010

(65) Prior Publication Data

US 2010/0312285 A1    Dec. 9, 2010

Related U.S. Application Data

(60) Provisional application No. 61/175,855, filed on May 6, 2009.

(51) Int. Cl.
*A61B 17/80* (2006.01)

(52) U.S. Cl. ..................................... 606/291; 606/289

(58) Field of Classification Search .............. 606/280, 606/286, 289, 291, 305, 208; 411/417, 437
See application file for complete search history.

(56) References Cited

U.S. PATENT DOCUMENTS

| | | | |
|---|---|---|---|
| 6,454,769 B2 | 9/2002 | Wagner et al. | |
| 6,613,053 B1 * | 9/2003 | Collins et al. | 606/293 |
| 6,955,677 B2 | 10/2005 | Dahners | |
| 7,695,472 B2 | 4/2010 | Young | |
| 7,955,364 B2 * | 6/2011 | Ziolo et al. | 606/308 |
| 2006/0235400 A1 * | 10/2006 | Schneider | 606/69 |
| 2006/0264946 A1 * | 11/2006 | Young | 606/69 |
| 2007/0043366 A1 | 2/2007 | Pfefferle et al. | |
| 2008/0119894 A1 * | 5/2008 | Ehrhardt et al. | 606/280 |
| 2008/0140130 A1 | 6/2008 | Chan et al. | |
| 2008/0234677 A1 | 9/2008 | Dahners et al. | |
| 2009/0192550 A1 | 7/2009 | Leung et al. | |
| 2009/0292318 A1 | 11/2009 | White et al. | |

FOREIGN PATENT DOCUMENTS

| | | |
|---|---|---|
| DE | 43 43 117 | 12/1993 |
| DE | 9321544 | 10/1999 |
| WO | 2008007196 | 1/2008 |
| WO | WO 2008007196 A2 * | 1/2008 |
| WO | 2009058969 | 5/2009 |

OTHER PUBLICATIONS

Partial European Search Report for Application No. 10162215.7 dated Jul. 10, 2010.

* cited by examiner

*Primary Examiner* — Kevin T Truong
*Assistant Examiner* — Christian Sevilla
(74) *Attorney, Agent, or Firm* — Michael F. Scalise (57) ABSTRACT

The present invention relates to a bone plate designed to secure locking screws inserted into the plate at various angles. The interior wall surface of the plate apertures include a series of protruding threaded ridges interspaced by relief notches. The threaded ridges and intermediate relief notches of the bone plate in combination with the threaded ridges and intermediate relief notches of the locking screw head allow the locking screw to bypass or "jump" threads of the bone plate. Thus, the locking screw can be inserted into the bone plate at a first angle and part-way through its advancement along the threads of the bone plate that angle can be changed. The second angle can either be greater than the first with respect to an orientation perpendicular to a longitudinal axis of the bone plate, or less than. This gives the physician a great amount of flexibility during a surgical procedure.

17 Claims, 9 Drawing Sheets

BONE PLATE ASSEMBLY

BACKGROUND OF THE INVENTION

1. Field of the Invention

The present invention is related generally to implantable orthopedic implants. More specifically, the present invention is related to implantable orthopedic bone plates used to reinforce fractured bones.

2. Prior Art

Orthopedic bone plates play a critical role in the healing process of broken bones. Once a bone has been fragmented, it is ideal for the broken bone fragments to be joined back together under compression to promote improved healing. The bone plate is a critical device that is used as a stabilizing bar to bridge the gap between bone fragments.

During surgery, a bone plate is inserted next to the fragmented bone of a patient. Compression screws are first placed through the bone plate. They are anchored into each of the bone fragments and tightened, pulling the bone fragments together under a compression load and against the plate. Once the compression screws are set in place, locking bone screws are inserted through the bone plate and anchored into the fragmented bone. The locking screws in conjunction with the bone plate secure the bone fragments together and the compression created by the compression screws ensures that they do not move. However, high tensile stresses are created when the bone fragments are fixated with the locking screws. These tensile stresses could damage the fragile bone fragments and impair the healing process. Bone plates, therefore, are a key element in the bone healing process.

Bone fragmentation, however, is unpredictable. As a result of a traumatic experience, a bone may fragment in multiple erratic locations and present itself in random orientations. Every patient's bones are unique; no two bones will fragment in the same manner in the same orientation. Nevertheless, traditional bone plate technology makes it difficult for a bone plate to be oriented in such a manner as to be utilized correctly for every trauma situation. Bone plates are rigid braces, typically composed of metal, which have historically been designed with fixed threaded holes through which some bone screws may not properly align with the matching bone fragment. In that respect, early bone plate technology comprised bone plates with preexisting threaded holes in combination with threaded locking screws. These earlier bone plates often lacked the ability to secure bone fragments that were not aligned under the threaded screw holes. That is because the preexisting threaded holes of earlier bone plate technology confined the angle through which the locking screw could be advanced into a bone fragment.

For example, with the earlier bone plate and screw technology, the physician could only advance the screw along the pre-defined orientation of the threads in the bone plate. This limitation often created a problem for the physician in that only bone fragments that presented themselves directly under a threaded aperture in the bone plate could be secured together. Examples of these earlier bone plate and locking screw devices are disclosed in U.S. Pat. No. 5,709,686 to Talus et al.; U.S. Pat. No. 6,206,881 to Frigg et al.; and U.S. Pat. No. 6,306,140 to Siddiqui, the disclosures of which are incorporated herein by reference.

In an effort to increase the degree of freedom in healing fractured bones, bone plates were developed with locking screws that can be inserted at different angles through the plate. One such improvement was the development of a bone plate with a tappable contact region as disclosed in U.S. Pat. No. 6,955,677 by Dahners. The disclosure of this patent is incorporated herein by reference. The '677 patent discloses a bone screw with a threaded head that is intended to penetrate into the hole of the bone plate in a tapping fashion. A drawback to this invention, however, is that it utilizes a softer bone plate material which lacks rigidity and stiffness to bear high tensile loads. Over time the softer material of the bone plate can yield to tensile stresses, resulting in possible movement of the bone fragments, which is detrimental to proper healing of the bone fragments.

Accordingly, an orthopedic device is needed that expands the possible locking screw insertion angles in anchoring bone fragments to promote bone healing.

SUMMARY OF THE INVENTION

In that light, the present invention is directed to an orthopedic bone plate system comprising a compression screw, a locking screw, and a bone plate with a plurality of complex locking screw apertures. The inner wall of the bone plate is provided with a plurality of thread columns separated from each other by relief notches. Likewise, the head of the locking screw is provided with a plurality of thread columns separated from each other by relief notches. When the thread columns of one are aligned with the relief notches of the other, it is possible to impart a lateral force to the screw. This force causes the screw threads to jump either up or down one row of threads on the bone plate to alter the angular orientation of the bone screw with respect to its original orientation when its threaded engagement with the bone plate began. That way, the present bone plate system increases the number of possible locking screw insertion angles even after the screw is partially threaded into the bone plate and the bone undergoing repair. This results in a desirable compression fit between plate and bone that would otherwise not be possible.

Therefore, it is now possible to secure bone fragments in compression with a bone plate using greater angular orientations for the bone screw.

BRIEF DESCRIPTION OF THE DRAWINGS

Figure 1:
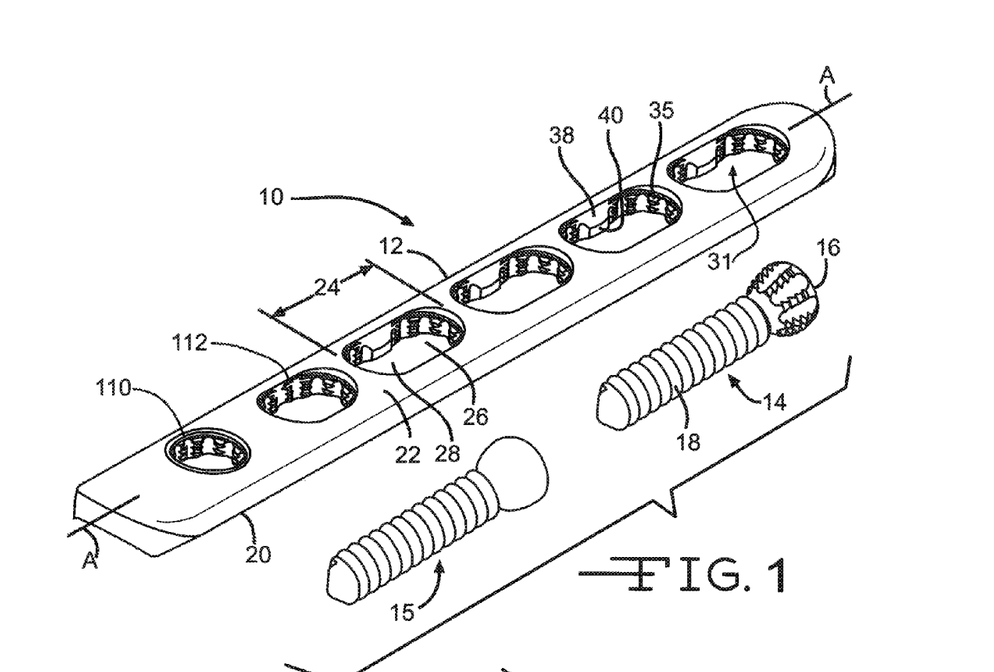
FIG. 1 is a perspective view of the orthopedic bone plate system 10 of the present invention.

Turning now to the drawings, FIG. 1 is a perspective view of an orthopedic bone plate system 10 according to the present invention. The bone plate system 10 comprises a bone plate 12 and at least one locking screw 14. If desired, at least one compression screw 15 can also be included.

Figure 2A:
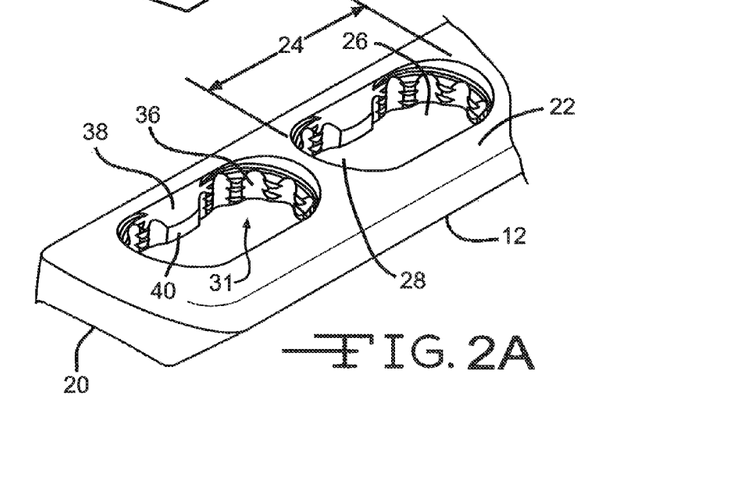
FIG. 2A is an enlarged view of two complex bone plate apertures of the present invention as shown in FIG. 1.
Figure 2B:
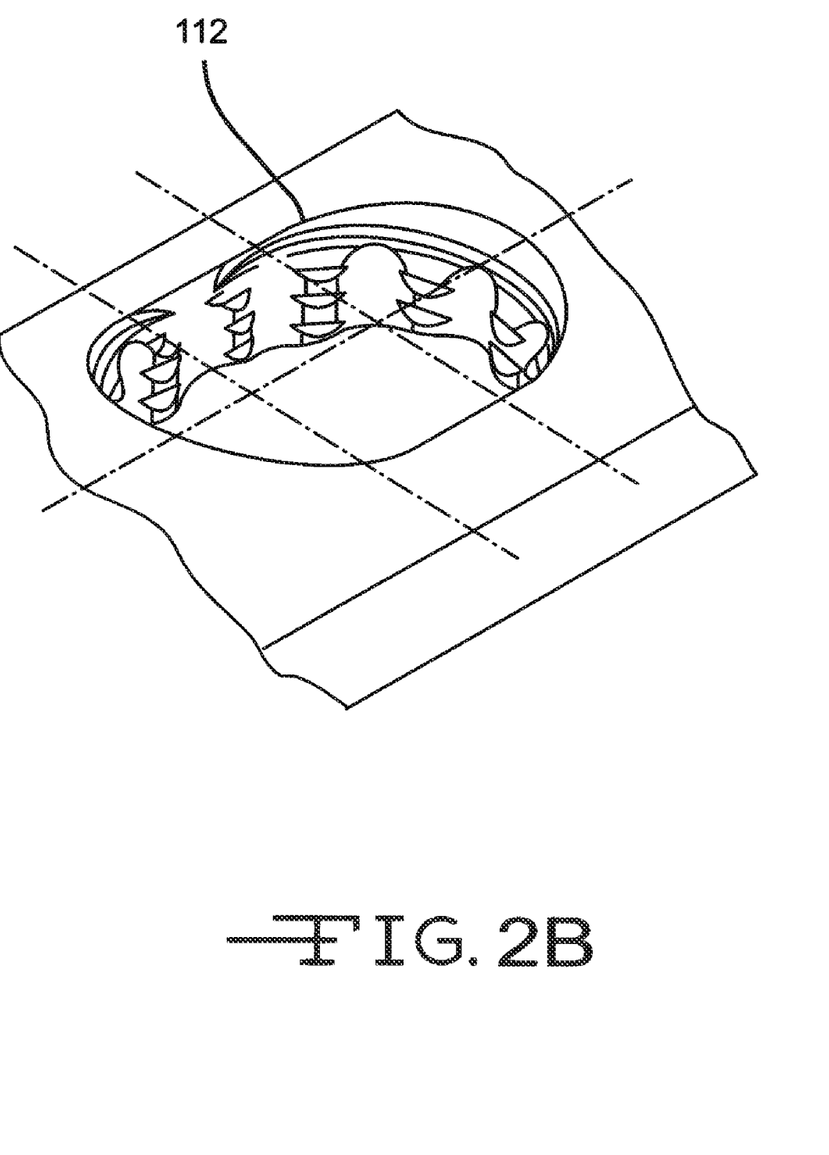
FIG. 2B is an enlarged view of a complex bone plate aperture 112 comprising overlapping holes meeting each other at a threaded overlap forming an hourglass shape as shown in FIG. 1.

The bone plate 12 has a longitudinal axis A-A, an axis B-B (FIG. 3) which is oriented 90 degrees from axis A-A, a bone contacting bottom side 20 and a top side 22. At least one complex aperture 24 extends through the bone plate 12 from the top side 22 to the bottom side 20. The complex aperture 24 is designed to receive either the locking screw 14 or the compression screw 15. In this embodiment, the complex aperture 24 is comprised of at least one set of two immediately adjacent apertures 26, 28. The apertures 26, 28 do not overlap, thereby providing the complex aperture 24 as an oval shaped opening. FIG. 2 shows an enlarged perspective view of the complex aperture 24.

Figure 3:
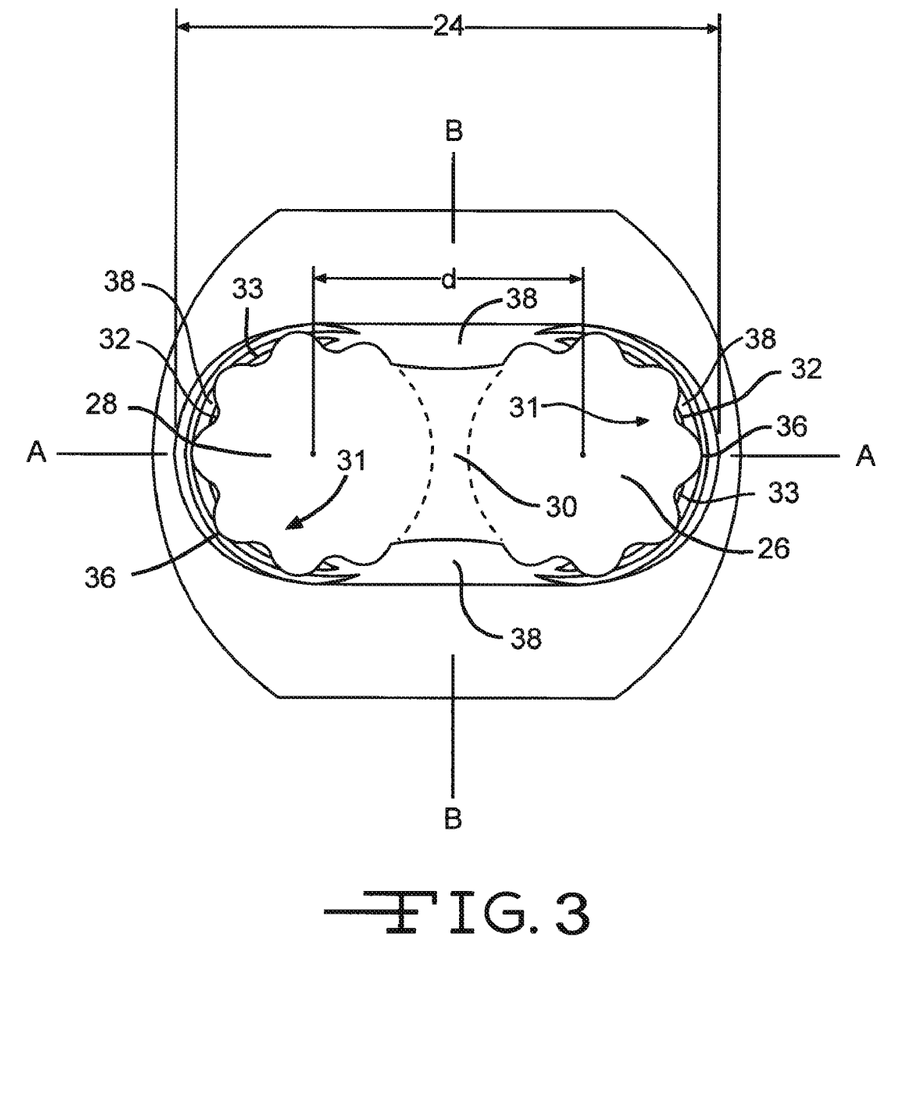
FIG. 3 is an enlarged top view of a complex bone plate aperture of the present invention.
Figure 9:
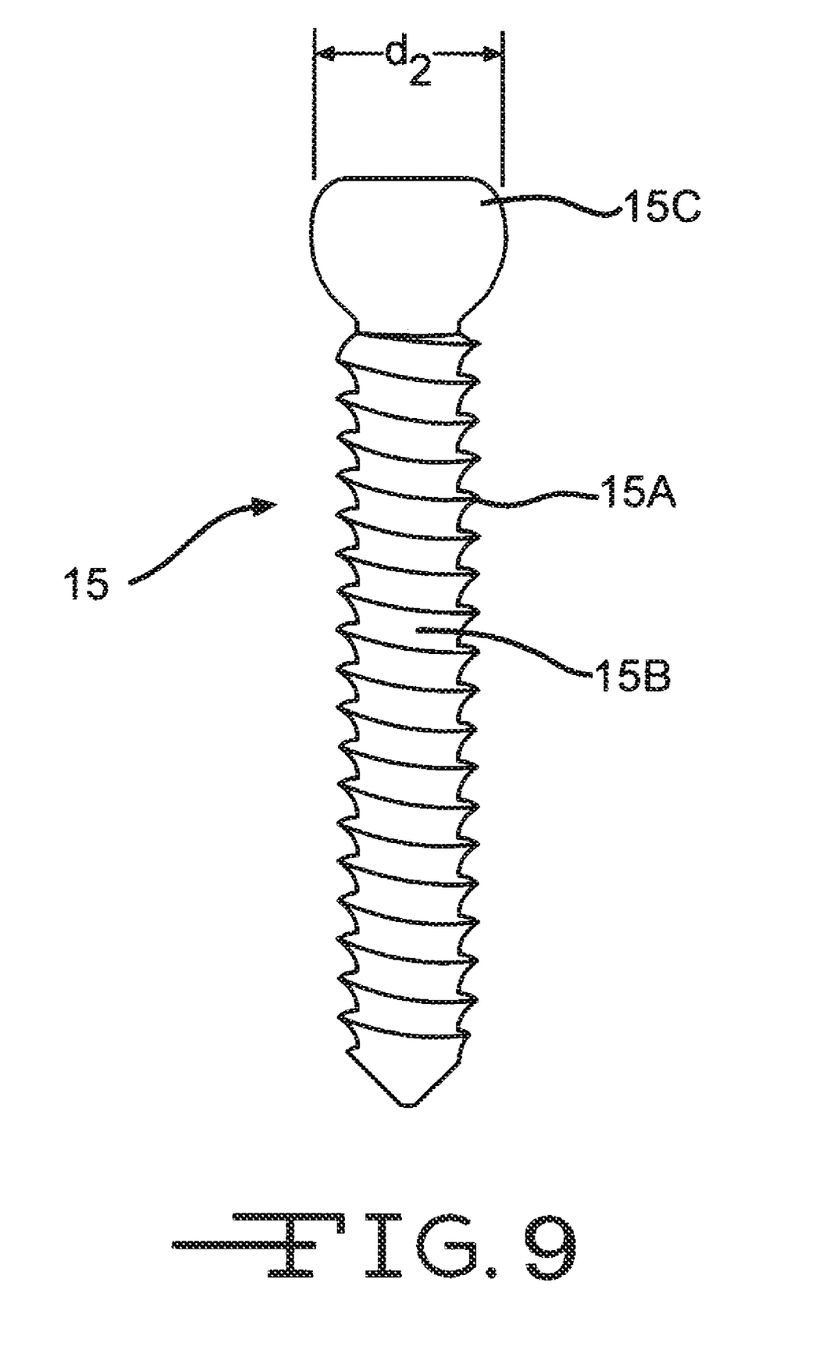
FIG. 9 is a perspective view of a compression screw.

The plan view of the complex aperture 24 illustrated in FIG. 3 shows that apertures 26, 28 have a center-to-center distance d along the longitudinal axis A-A that is greater than the diameter $d_1$ of the head of the locking screw 14 (FIG. 4A) or $d_2$ of the head of the compression screw 15 (FIG. 9). That way, the adjacent apertures 26, 28 of the complex aperture 24 define a relief-space 30 disposed between them. Preferably, the relief-space 30 is configured as either a straight slot, or as a constricted or "waisted" slot centered along axes A-A and bisected by axis B-B.

A compression ramp surface 38 emerges into the complex aperture 24 from opposite sides of the wall 34 of the bone plate 12 to provide part of the boundary for the relief-space 30. Preferably, the compression ramp surfaces 38 are non-threaded and ramp into the open relief space 30 of the complex aperture 24 along both the axis B-B perpendicular to the longitudinal axis A-A of the bone plate 12 and into the open space of the openings 26, 28 themselves. The ramp surfaces 38 slope downwardly and inwardly from the bone plate top side surface 22 into the opening of the complex aperture 24. At the relief space 30, the distal end of each of the ramps 38 meets a substantially vertical, surface 40 which extends to the bone plate bottom side 20. At the openings 26, 28, the ramps 38 meet threaded surfaces of the openings. Vertical surface 40 can be planar or have a beveled contour that ramp into the open spaces 30 and into each of the apertures 26, 28 of the complex aperture 24.

The downwardly and inwardly sloping ramps 38 act as compression structures for the locking screw 14. As the locking screw 14 is threaded into one of the apertures 26 or 28 comprising the complex aperture 24 and moves in a downwardly direction, the underside of the locking screw head 16 compresses against the ramp surface 38. The downwardly sloping inclination of the ramp 38 causes the screw head 16 to slide down the ramp 38, creating a frictional fit and prohibiting advancement of the locking screw 14 further into the complex aperture 24.

A series of threads that are generally indicated by numerical designation 31 in FIGS. 1 and 2 protrude from the plate walls defining the apertures 26, 28. The plate threads 31 are aligned in a spiral extending from adjacent to the top side 22 toward the bottom side 20. The spiral of the plate threads 31 has a pitch that ranges from about 0.1 mm. to about 1.0 mm.

Figure 6:
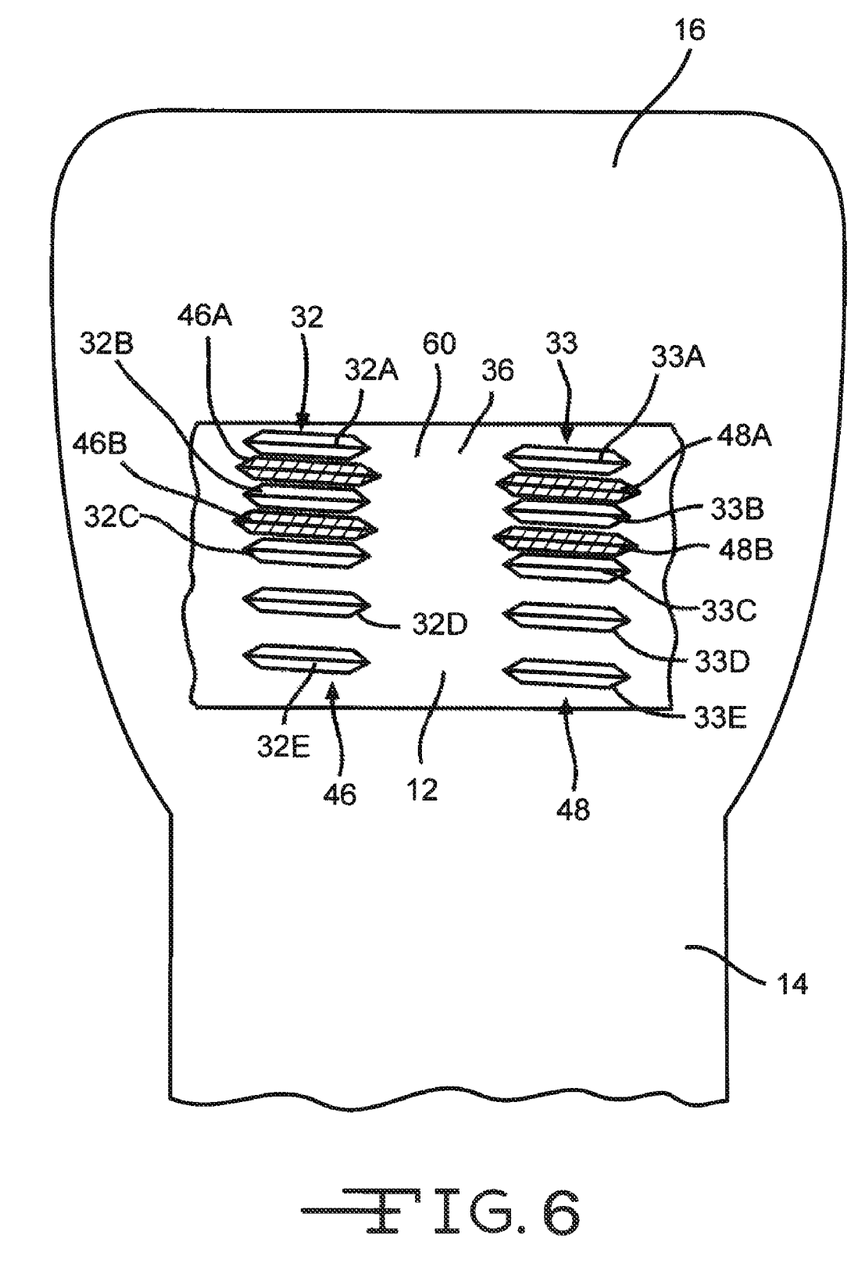
FIG. 6 is a schematic view depicting the advancement of a screw through a threaded aperture of a bone plate at a first angle.
Figure 7:
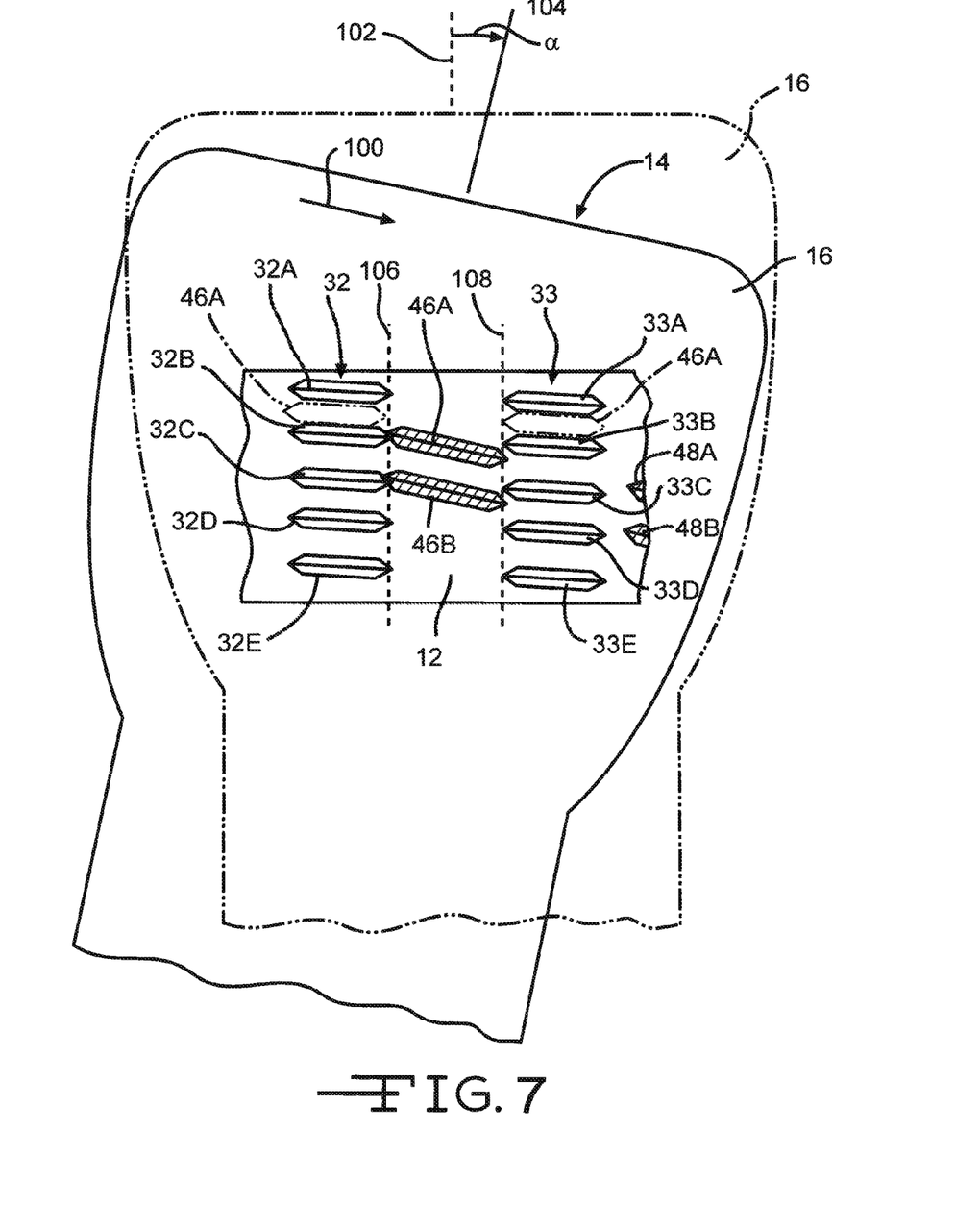
FIG. 7 is a schematic view showing the threads of the screw of FIG. 6 having "jumped" a row of threads in the bone plate to change the orientation of the screw to a second, different angle.
Figure 8:
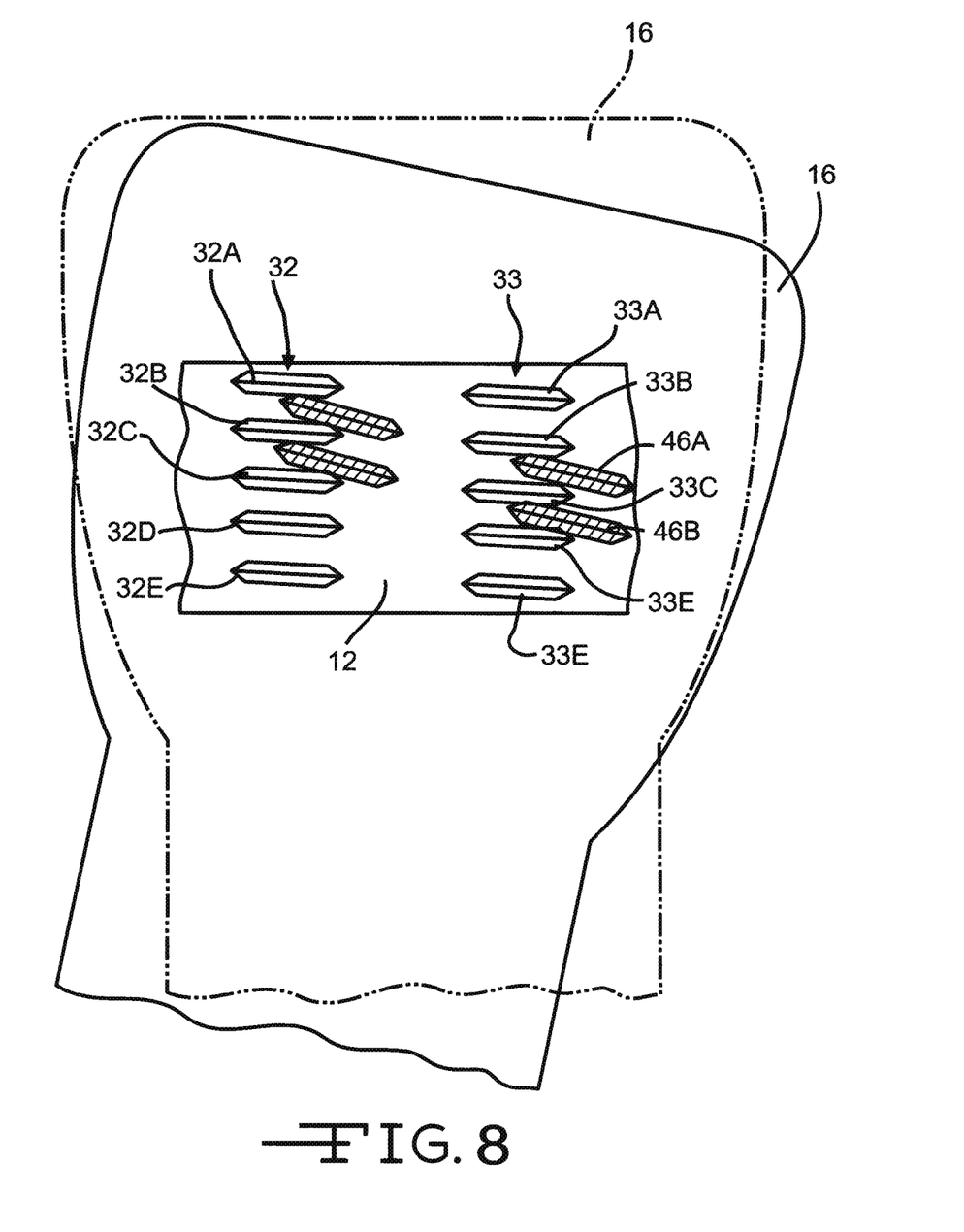
FIG. 8 is a schematic view showing the locking screw being threaded into the plate at the second angle depicted in FIG. 7.

The plate threads 31 are also orientated in thread columns 32, 33, etc. (FIGS. 6 to 8). Each thread column 32, 33 extends along the interior aperture wall surface 34 from the top side 22 to the bottom side 20 of plate 12. The thread columns 32, 33 are preferably spaced apart from each other by a distance ranging from about 0.10 mm. to about 0.500 mm.

The space between each thread column 32, 33 is defined as an aperture relief notch 36 in the form of an indentation into the wall of the bone plate 12 defining the apertures 26, 28 of the complex aperture 24. Each complex aperture 24 may comprise multiple relief notches 36 having exemplary shapes including curved, squared-off or as a key slot. In that manner, the threads 31 of the bone plate 12 provide both spiral and columnar structures.

Figure 4:
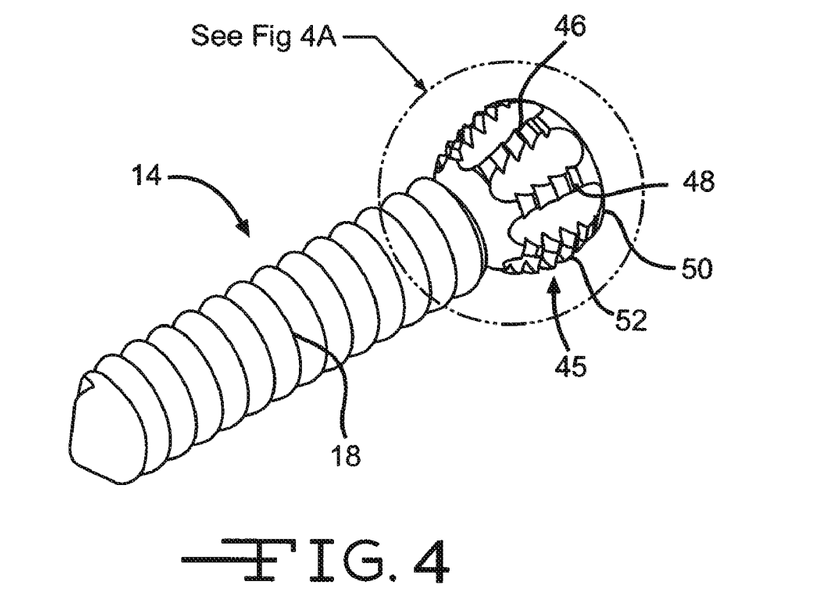
FIG. 4 is a perspective view of a locking screw embodiment of the present invention.
Figure 4A:
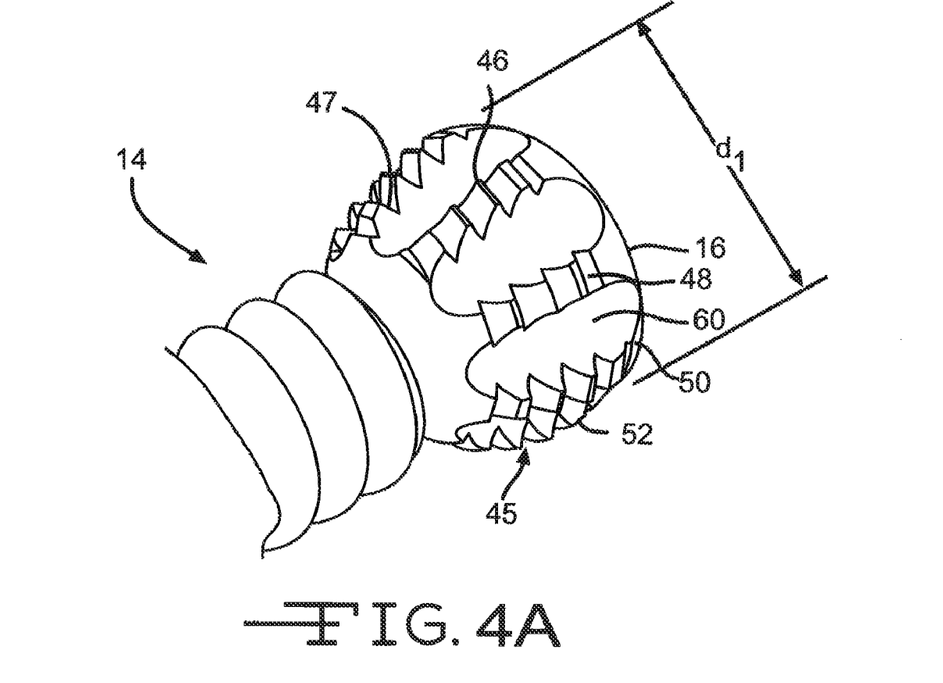
FIG. 4A is an enlarged perspective view of the locking screw head as shown in FIG. 4.

As shown in FIGS. 4 and 4A, the locking screw 14 is comprised of a bulbous head 16 and an elongated shaft 18. The locking screw head 16 is comprised of locking threads that are generally indicated by numerical designation 45. The threads have a pitch similar to that of the threads 31 of the bone plate 12. The screw threads 45 are also aligned in a series of threaded columns 46, 48, 50, 52, 54 (numerical designation 54 is only shown in FIG. 5), etc. When viewed from the side, the locking threads 45 are separated from each other by a "V" cutout 47. It is in the space provided by the V-cutouts 47 that the threads 31 of the bone plate 12 reside as the screw 14 is threaded into the bone plate. A screw relief notch 60 is provided between adjacent columns of locking threads 45. The relief notches 60 extend from the locking screw head proximal end to the locking screw head distal end adjacent to the threaded shaft 18.

Figure 5:
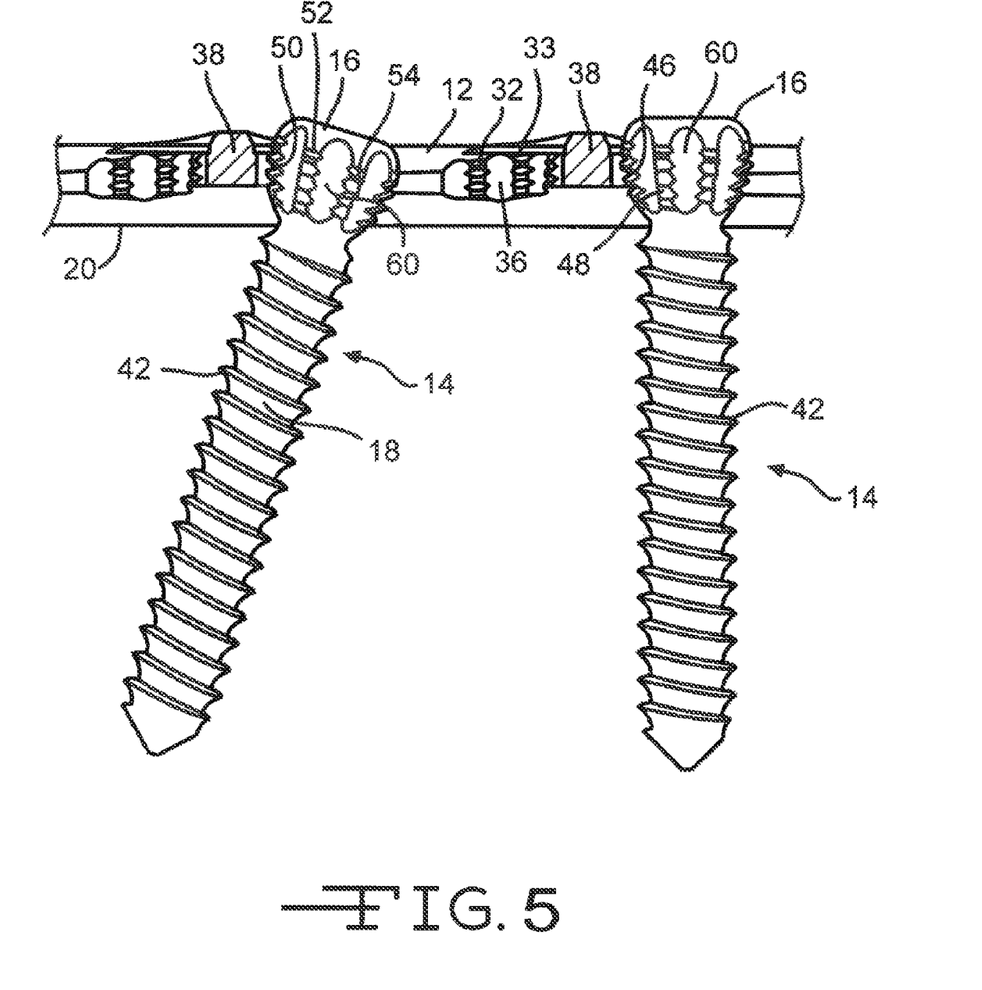
FIG. 5 depicts a cross-sectional view of the present invention with locking screws inserted through the bone plate of the present invention.

FIG. 5 illustrates two exemplary orientations of locking screws 14 threaded in the bone plate 12. The right one is at about 90 degrees with respect to the longitudinal plane of the bone plate 12 while the left locking screw 14 is at an insertion angle of about 10° in relation to the longitudinal plane. Insertion angles can range from about 1° to about 45°, however, they preferably range from about 10° to about 40°, and more preferably from about 15° to about 35° from perpendicular. This figure is an exemplary illustration of the many orientations that the locking screw 14 can be inserted into the bone plate 12.

FIGS. 6, 7 and 8 illustrate how the present bone plate 12 and locking screw 14 system 10 allows the threads of the locking screw head 16 to bypass or "jump" threads on the bone plate. That the threads of the locking screw head 16 are capable of "jumping" threads of the bone plate 12 is made possible by the incorporation of the respective relief notches 36, 60 in both the bone plate apertures 26, 28 of the complex aperture 24 and in the locking screw head 16.

As FIG. 6 shows, as the locking screw 14 is threaded into the bone plate 12, screw threads in column 46 and 48 reside between thread columns 32 and 33, respectively, of the bone plate. In other words, the threads of the bone plate columns 32, 33 reside in the cutouts 47 provided between the thread columns 46, 48 of the screw 14.

In particular, screw thread 46A resides between bone plate threads 32A and 32B and screw thread 46B resides between bone plate threads 32B and 32C. In the adjacent column, screw thread 48A resides between bone plate threads 33A and 33B and screw thread 48B resides between bone plate thread 33B and 33C. The relief notch 36 of the bone screw 12 resides between screw thread columns 32 and 33 and relief notch 60 of the plate 12 resides between plate thread columns 46 and 48. This alignment of the screw threads disposed between threads of the bone plate 12 is a typical configuration as the locking screw 14 is threaded into the bone plate in a customary manner. In particular, since the plate threads have a pitch, plate thread 33A is at a slightly lower elevation than plate thread 32A as the screw 16 is advancing into the bone plate. That is regardless whether the locking screw 14 is at an initial orientation perpendicular to the longitudinal plane of the plate as in the right-hand screw shown in FIG. 5 or at some other angular orientation as shown in the left-hand screw in that drawing.

FIG. 7 illustrates how the locking screw threads bypass or "jump" levels of bone plate threads. As the figure shows, a lateral force 100 has been applied to the locking screw head

16. This lateral force 100 is illustrated by showing that the longitudinal axis of the screw 16 has deviated an angle α. This angle is measured by the difference between the longitudinal axis 102 of the screw prior to the lateral force 100 in relation to the orientation of the axis 104 after the lateral force. In practice, the lateral force 100 would be imparted to the screw as the screw is simultaneously being threaded into the bone plate.

As a result of the lateral force 100, exemplary locking screw thread 46A has moved laterally and downwardly, bypassing or "jumping" from where it would have resided between bone plate threads 33A and 33B had the lateral force 100 not occurred to being angled toward a position residing between bone plate threads 33B and 33C (FIG. 8). This lateral force can only be exerted against the screw 14 when its columns of threads reside in the notches 36 of the bone plate 12. That is when the leading edge of a screw thread, for example threads 46A and 46B, is not engaged with either thread column 32 or 33 of the bone plate. However, the trailing edge of the screw threads 46A, 46B are still disposed between bone plate threads 32A, 32B and 32B, 32C, respectively. Otherwise, the bone screw 14 would be capable of simply "falling" through the bone plate every time the columns of threads 46, 48, 50, 52, 54, etc. on the screw 14 are in alignment with the relief notches 36 of the plate 12.

Further, the width of each thread 45 comprising the thread columns 46, 48, 50, 52, 54, etc. of the screw 14 are laterally from about 0.5 to 2 millimeters wider than the width of the bone plate relief notches 36. This is illustrated in FIG. 7 where exemplary screw thread 46A has its leading edge just beginning to reside between the edges of plate threads 33B, 33C before the trailing edge of that thread has left the edges of plate threads 32A, 32B. That is from a longitudinal perspective with respect to the edges of the threads of the plate 12 and of the screw 14 as shown, by dashed lines 106 and 108.

It should be pointed out that while the present plate and screw system 10 permits the physician to change the angle of the screw 14 part way through it being screwed into the plate 12, that should not be viewed as limiting. Additionally, the screw 14 could be oriented with the threads of the bone plate 12 in the orientation shown in FIG. 8. That is in a "jumped" or cross-threaded orientation from the beginning. Furthermore, even though the sequence of drawings of FIGS. 6 to 8 shown that the angle α can be increased so that the screw ends at a greater angle of inclination that which it was first oriented (FIG. 6), the angle could also be decreased. That would be where even though the screw is being tightened by being rotated to the right, the angle of inclination or pitch of its threads is in an upwardly or horizontal orientation instead of a downwardly direction as shown in FIG. 8. This structure provides the physician with a large amount of flexibility in repairing a fractured bone with the present system 10.

The compression screw 15 illustrated in FIG. 9 can also be used with the bone plate 12 of the present invention. The compression screw 15 has shaft threads 15A that are helically disposed around the shaft 15B. An unthreaded head 15C is affixed to the proximal end of the shaft 15B.

The bone plate 12 and locking and compression screws 14, 15 are preferably made from Ti 6Al-4V. However, other biocompatible materials, not limited to other titanium alloys, stainless steel or polymers, i.e., PEEK could also be used.

FIG. 1 further illustrates that the bone plate can comprise a threaded aperture 110 adapted to receive only one screw or an overlapping threaded aperture 112. The overlapping threaded aperture is similar to that described in U.S. Pat. No. 7,695,472 to Young, which is incorporated herein by reference. The complex aperture 112 comprises at least two overlapping holes having an offset of a given distance between centers thereof, wherein any two immediately adjacent overlapping holes comprise a compression ramp extending from an oval shaped opening at the top side of the plate downwardly and inwardly part way through the plate thickness to a threaded lower portion having an hourglass shape extending from where the compression ramp ends at the hourglass shape to the bottom side of the bone plate with threaded surfaces of the overlapping holes meeting each other at a threaded overlap forming the hourglass shape, wherein the threaded lower portion is adapted to lock with threads of a corresponding bone screw in one or the other of the overlapping holes. The overlapping holes can be formed either normal to the top side of the plate or at an angle offset from normal. In either embodiment 110, 112, the aperture has a relief notches disposed between columns of threads as described with respect to the complex aperture 24.

It is appreciated that various modifications to the inventive concepts described herein may be apparent to those of ordinary skill in the art without departing from the spirit and scope of the present invention.

What is claimed is:

1. A bone plate system, which comprises:
    a) an elongated plate having a longitudinal axis, a bone contacting bottom side, a topside, a thickness between the topside and the bottom side and at least one threaded screw aperture comprising plate threads, wherein the plate threads are provided with a first pitch and comprise a first plurality of threaded columns separated by first intermediate relief notches;
    b) a screw comprising a shaft provided with shaft threads that are adapted to thread into a bone, the shaft supporting a head provided with screw head threads, wherein the screw head threads are provided with a pitch substantially matching the first pitch of the plate threads and comprise a second plurality of threaded columns separated by second intermediate relief notches; and
    c) wherein a width of each screw head thread comprising the second plurality of threaded columns of the screw head is wider than the width of the first intermediate relief notches of the plate, and
    d) wherein during use, the screw is threadable into a threaded engagement with the threaded aperture of the bone plate with the screw head threads being in a contact relationship with the plate threads at a first pitch and further wherein the screw is manipulatable by imparting a lateral force thereto to cause the screw to change its angle of inclination with respect to the plate from a first inclination to a second inclination when the screw head threads substantially reside in the first intermediate relief notches between adjacent first threaded columns so that the screw head threads are moved from being in a first threaded engagement with a first thread of the plate threads to subsequently being in a second threaded engagement with a second plate thread, the second plate thread being either one thread up or one thread down along the longitudinal axis of the at least one threaded screw aperture of the bone plate.

2. The bone plate system of claim 1 wherein the first plurality of threaded columns extend from adjacent the topside toward the bottom side of the bone plate.

3. The bone plate system of claim 1 wherein the second plurality of threaded columns extend substantially along a longitudinal axis of the screw.

4. The bone plate system of claim 1 wherein the at least one threaded screw aperture in the plate is sized to receive only one screw.

5. The bone plate system of claim 4 wherein the at least one threaded screw aperture in the plate is a complex aperture comprising first and second threaded apertures separated from each other by a relief zone.

6. The bone plate system of claim 4 wherein the at least one threaded screw aperture in the plate is a complex aperture extending through the plate thickness and comprised of at least two overlapping holes having an offset of a given distance between centers thereof, wherein any two immediately adjacent overlapping holes comprise a compression ramp extending from an oval shaped opening at the top side of the plate downwardly and inwardly part way through the plate thickness to a threaded lower portion having an hourglass shape extending from where the compression ramp ends at the hourglass shape to the bottom side of the bone plate with threaded surfaces of the overlapping holes meeting each other at a threaded overlap forming the hourglass shape, wherein the threaded lower portion of the complex aperture comprises the plate threads provided with the first pitch and comprising the first plurality of threaded columns separated by the first intermediate relief notches.

7. The bone plate system of claim 1 wherein the plate and screw are made from a biocompatible metal or polymer.

8. The bone plate system of claim 1 wherein the plate and screw are part of a kit.

9. The bone plate system of claim 8 wherein the kit includes both a locking screw and a compression screw.

10. The bone plate system of claim 1 wherein the plate threads extend through the thickness thereof.

11. The bone plate system of claim 6 wherein the complex aperture is adapted to lock with threads of the bone screw in one or the other of the overlapping holes.

12. A bone plate system, which comprises:
a) an elongated plate having a longitudinal axis, a bone contacting bottom side, a topside, a thickness between the topside and the bottom side and at least one complex aperture extending through the plate thickness, the complex aperture comprised of at least two overlapping holes having an offset of a given distance between centers thereof, wherein any two immediately adjacent overlapping holes comprise a compression ramp extending from an oval shaped opening at the top side of the plate downwardly and inwardly part way through the plate thickness to a threaded lower portion having an hourglass shape extending from where the compression ramp ends at the hourglass shape to the bottom side of the bone plate with threaded surfaces of the overlapping holes meeting each other at a threaded overlap forming the hourglass shape, wherein the threaded lower portion of the complex aperture comprises plate threads provided with a first pitch and comprising a first plurality of threaded columns separated by first intermediate relief notches;
b) a screw comprising a shaft provided with shaft threads that are adapted to thread into a bone, the shaft supporting a head provided with screw head threads, wherein the screw head threads are provided with a pitch substantially matching the first pitch of the plate threads and comprise a second plurality of threaded columns separated by second intermediate relief notches; and
c) wherein a width of each screw head thread comprising the second plurality of threaded columns of the screw head is wider than the width of the first intermediate relief notches of the plate, and
d) wherein during use, the screw is threadable into a threaded engagement with the threaded aperture of the bone plate with the screw head threads being in a contact relationship with the plate threads at a first pitch and further wherein the screw is manipulatable by imparting a lateral force thereto to cause the screw to change its angle of inclination with respect to the plate from a first inclination to a second inclination when the screw head threads substantially reside in the first intermediate relief notches between adjacent first threaded columns so that the screw head threads are moved from being in a first threaded engagement with a first thread of the plate threads to subsequently being in a second threaded engagement with a second plate thread, the second plate thread being either one thread up or one thread down along the longitudinal axis of the at least one threaded screw aperture of the bone plate.

13. The bone plate system of claim 12 wherein the complex aperture is adapted to lock with threads of the bone screw in one or the other of the overlapping holes.

14. A bone plate system, which comprises:
a) an elongated plate having a longitudinal axis, a bone contacting bottom side, a topside, a thickness between the topside and the bottom side and at least one threaded screw aperture comprising plate threads, wherein the plate threads are provided with a first pitch and comprise a first plurality of threaded columns separated by first intermediate relief notches;
b) a screw comprising a shaft provided with shaft threads that are adapted to thread into a bone, the shaft supporting a head provided with screw head threads, wherein the screw head threads are provided with a pitch substantially matching the first pitch of the plate threads and comprise a second plurality of threaded columns separated by second intermediate relief notches; and
c) wherein a width of each screw head thread comprising the second plurality of threaded columns of the screw head is wider than the width of the first intermediate relief notches of the plate, and
d) wherein during use, the screw is threadable into a threaded engagement with the threaded aperture of the bone plate with the screw head threads being in a contact relationship with the plate threads at a first pitch and further wherein the screw is manipulatable by imparting a lateral force thereto to cause the screw to change its angle of inclination with respect to the plate from a first inclination to a second inclination when the screw head threads substantially reside in the first intermediate relief notches between adjacent first threaded columns so that the screw head threads are moved from being in a first threaded engagement with a first thread of the plate threads to subsequently being in a second threaded engagement with a second plate thread, the second plate thread being either thread up or thread down along the longitudinal axis of the at least one threaded screw aperture of the bone plate.

15. The bone plate system of claim 1 wherein the width of each screw head thread comprising the second plurality of threaded columns of the screw is from 0.5 to 2 millimeters wider than the width of the first intermediate relief notches of the plate.

16. The bone plate system of claim 12 wherein the width of each screw head thread comprising the second plurality of threaded columns of the screw is from 0.5 to 2 millimeters wider than the width of the first intermediate relief notches of the plate.

17. The bone plate system of claim 14 wherein the width of each screw head thread comprising the second plurality of threaded columns of the screw is from 0.5 to 2 millimeters wider than the width of the first intermediate relief notches of the plate.

* * * * *